United States Patent [19]

Kenyhercz et al.

[11] Patent Number: 5,627,152

[45] Date of Patent: May 6, 1997

[54] METHOD FOR INCREASING BODYWEIGHT

[75] Inventors: Thomas M. Kenyhercz, Hillsborough, N.J.; Ellen D. Jorgensen, Pound Ridge, N.Y.

[73] Assignee: Telluride Pharmaceutical Corporation, Hillsborough, N.J.

[21] Appl. No.: 374,187

[22] Filed: Jan. 18, 1995

[51] Int. Cl.$^6$ ................................................. A61K 38/00
[52] U.S. Cl. ........................................................... 514/2
[58] Field of Search ........................................... 514/2

[56] References Cited

FOREIGN PATENT DOCUMENTS

92/21368  12/1992  WIPO.

Primary Examiner—Raymond Henley, III

[57] ABSTRACT

The present invention is directed to a method for increasing lean body weight in a mammal or for the treatment or prophylaxis of abnormal weight loss such as cachexia in a mammal through the administration of a composition containing glutathione.

7 Claims, No Drawings

METHOD FOR INCREASING BODYWEIGHT

FIELD OF THE INVENTION

The present invention relates to a method of increasing bodyweight.

BACKGROUND OF THE INVENTION

There has been for many years a demand for safe and effective methods by which people who wish to appear more physically attractive by gaining lean body mass can increase their bodyweight. Likewise, there is a need for a safe and effective prophylaxis and treatment of pathological weight loss which often accompanies disease or illness and which presents a genuine danger to health.

Though many methods of increasing weight exist which involve bodybuilding regimens (such as repetitive lifting of weights), they are of limited value when the individual is either insufficiently motivated or physically unable due to debilitating illness to adhere to such an exercise regimen. Through carefully controlled diets it is possible to effect healthy weight gain, however many people find it difficult to adhere to such regimens, and those suffering from cachexia (abnormal weight loss) may be unable to ingest such diets easily. Therefore there exists a need for a safe, effective and convenient method for increasing bodyweight.

Glutathione is a tripeptide best known for its antioxidant properties. For the avoidance of doubt the substance referred to herein above as glutathione is the compound:

-L-glutamyl-cysteinylglycine (oxidized or reduced form)

and having the chemical formula:

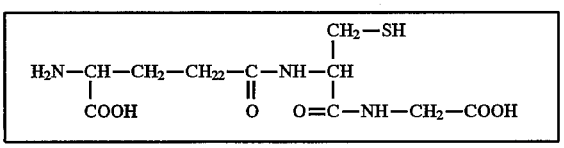

(in the case of the reduced form).

Glutathione is relatively inexpensive and is readily available. It commonly exists as a water-soluble whitish powder which can be encapsulated, tableted, or dissolved in liquid to make an oral or aerosol dosage form. The physical and chemical characteristics of glutathione have been described in the Merck Index, 11th Ed., page 703.

Its uses as a food preservative, in cosmetics, as an antidote to the poisoning effect of heavy metals, in cancer chemotherapy, as an antiviral and anti-inflammatory, to treat hepatic disorders and necrosis, to treat pulmonary dysfunction and sickle cell disease, to prevent and treat restenosis following angioplasty, to lower plasma lipoprotein levels, and to treat ischemic heart disease have been previously disclosed. See, for example, U.S. Pat. Nos. 3,146,165, 4,229,468, 4,689,347, 4,758,551, 4,762,705, 4,871,528, and 4,927,850, 5,108,754, 5,204,114, 5,272,166, 5,238,683, 5,326,757.

U.S. Pat. No. 4,466,978 describes the use of glutathione to reduce bodyweight, but gives no examples of this. The authors have found that, unexpectedly, treatment with glutathione produced the opposite effect, namely causing an increase in bodyweight.

The use of glutathione as one component of a multicomponent nutritional formulation to treat patients suffering from acquired immunodeficiency syndrome (henceforth referred to as AIDS) and AIDS-related complex is disclosed in WO #92/21368. In one example from WO #92/21368 two out of three patients treated with the multicomponent nutritional formulation showed increased bodyweight after treatment. The authors have discovered that the use of glutathione alone can effect an increase in bodyweight, without the need for the additional components of the composition described in WO #92/21368.

OBJECT AND SUMMARY OF THE PRESENT INVENTION

It is an object of the present invention to provide a safe, effective, convenient method for increasing bodyweight which is free from the inconveniences of presently known methods for weight gain. The present invention provides in one aspect a method of weight gain and in a further aspect a method for the prophylaxis and treatment of cachexia, or abnormal weight loss.

It has been discovered, quite unexpectedly, that the administration of glutathione alone can increase bodyweight. This finding is particularly surprising in light of reports that the administration of a nutritional composition containing multiple ingredients including glutathione was required to effect weight gain in AIDS patients (WO #92/21368), and that the administration of glutathione alone has been reported to promote the opposite effect, namely weight loss, in overweight persons (U.S. Pat. No. 4,466,978). High doses of glutathione have previously been reported to promote cachexia in guinea pigs (Martensson, J. et al, Proc. Natl. Acad. Sci., USA 90: 317-321 1993).

In accordance with one aspect of the present invention, there is provided a method of increasing lean bodyweight comprising the step of administering, in each 24 hour period, an amount of glutathione, glutathione bioprecursors, physiological salts or esters thereof, effective to increase bodyweight.

In accordance with this aspect of the present invention, there is provided the method of increasing lean bodyweight as previously described wherein the glutathione is provided in an amount of between about 500 and about 5000 mg.

In a preferred embodiment in accordance with this aspect of the present invention the glutathione is administered in two substantially equal dosages, each of which is administered between about 8 and about 12 hours apart.

In a more preferred embodiment in accordance with this aspect of the present invention the glutathione is administered in three substantially equal dosages, each of which is administered between about 4 and about 8 hours apart.

In a most preferred embodiment in accordance with this aspect of the present invention the glutathione is administered in four substantially equal dosages, each of which is administered between about 3 and about 8 hours apart.

In accordance with another aspect of the present invention, there is provided the method of preventing and treating weight loss comprising the step of administering, in each 24 hour period, an amount of glutathione effective to prevent and to treat weight loss.

In accordance with this aspect of the present invention, there is provided the method of preventing and treating weight loss as previously described wherein the glutathione is provided in an amount of between about 500 and about 5000 mg in each 24 hour period.

In a preferred embodiment in accordance with this aspect of the present invention the glutathione is administered in two substantially equal dosages, each of which is administered between about 8 and about 12 hours apart.

In a more preferred embodiment in accordance with this aspect of the present invention the glutathione is administered in three substantially equal dosages, each of which is administered between about 4 and about 8 hours apart.

In a most preferred embodiment in accordance with this aspect of the present invention the glutathione is administered in four substantially equal dosages, each of which is administered between about 3 and about 8 hours apart.

The aforementioned methods result from the discovery that the administration of glutathione, when provided to the body in sufficient quantity spaced throughout a 24-hour period, increases bodyweight and aids in the prevention and treatment of weight loss. While not wishing to be bound by any particular theory of operation, it is believed by the authors that glutathione acts to stimulate the appetite and increase healthy metabolism. It is further postulated that the ingestion of adequate amounts of glutathione are crucial for maximally efficient production of body proteins which make up muscle tissue. Glutathione has been shown to be necessary for correct folding of proteins in the endoplasmic reticulum, and lack thereof could possibly retard the formation of muscle mass.

DETAILED DESCRIPTION OF THE PREFERRED EMBODIMENT

In the preferred embodiment of the invention, the glutathione is administered in the form of a pharmaceutical formulation consisting of glutathione together with a pharmaceutically acceptable carrier therefor.

The carrier must be "acceptable" in the sense of being compatible with other ingredients of the formulation and not deleterious to the patient. Such carriers may be solid, liquid or gaseous materials suitable for the purpose of administering the formulation by the desired route.

These pharmaceutical formulations may be administered orally or parenterally (including subcutaneous, intramuscular, and intravenous injection) or as a suppository or pessary. In a more preferred embodiment of the invention, the formulation is administered orally.

For oral administration the pharmaceutical formulation may be administered in the form of a draught in water or in a syrup, in capsules, cachets, boluses or tablets, as an aqueous or oleaginous solution or suspension or in suspension as a syrup, such suspensions optionally including suspending agents, or as an oil-in-water or water-in-oil emulsion. Flavoring, coloring, sweetening, preserving, thickening or emulsifying agents may also be included in the formulation.

In a most preferred embodiment of the invention, the active ingredient is administered orally in the form of a capsule or tablet.

Tablets may contain glutathione as a powder or granules optionally mixed with binders, lubricants, inert diluents or surface-active or dispersing agents and may be formed by compression or molding in inert liquid diluent. Such tablets may be scored and/or coated.

Capsules and cachets may contain glutathione alone or in admixture with one or more other ingredients. Capsules may also contain glutathione in aqueous or oleaginous solution or suspension or emulsion optionally in association with other ingredients.

For administration in tablets and capsules as described above, glutathione is preferably present at from about 100 to about 1000 mg, most preferably from about 200 to about 750 mg per capsule or tablet.

All of the above formulations may be produced by standard processes comprising bringing the active ingredient into association with one or more pharmaceutically acceptable carriers.

The required effective dosage of glutathione will depend upon various factors such as the general health of the individual being treated, the severity and duration of previous weight loss causing the underweight condition, and the responsiveness of the individual patient to the treatment regimen. In a preferred embodiment of the invention, glutathione is administered at a dosage in the range of from 10 mg/kg bodyweight per day to 100 mg/kg bodyweight per day. In a more preferred embodiment of the invention glutathione is administered at a dosage of from 10 mg/kg bodyweight per day to 50 mg/kg bodyweight per day. In a most preferred embodiment of the invention the glutathione is administered as described above in four substantially equal dosages, each of which is administered between about 3 and about 8 hours apart.

Further preferred features of the invention will appear from the following examples.

EXAMPLE 1

A thirty-nine-year-old healthy female subject who wished to gain more weight in the form of lean muscle tissue, was treated for five weeks with one capsule containing 250 mg glutathione four times daily resulting in a total daily dosage of 1000 mg glutathione. The patient's weight at the start of treatment was 125 pounds (56.8 kg), and her percent bodyfat was measured by the caliper method to be 20.1%. This corresponds to 100 pounds of muscle, bone and connective tissue, and 25 pounds of fat. At the end of the five week treatment period, the subject weighed 129 pounds and her percentage bodyfat was measured to be 18.6%, which corresponds to 24 pounds of fat and 105 pounds of muscle, bone and connective tissue. The percent change in lean bodyweight, a 5% gain, is particularly significant, as it was accomplished without a change in diet or exercise regimen.

EXAMPLE 2

A forty-three-year-old healthy male subject who wished to add bodyweight in the form of lean muscle, was treated for seven weeks with one capsule containing 500 mg of glutathione, four times per day. The totally daily dose was 2,000 mg of glutathione. The patient weighed 220 pounds (100 kg) at the initiation of the treatment, and his percent bodyfat was measured by the caliper method to be 24.9%. This corresponds to 165 pounds of muscle, bone and connective tissue, and 55 pounds of fat. At the end of the seven week treatment period, the subject weighed 248 pounds and his percentage bodyfat was measured to be 22.3%. This corresponds to 55 pounds of fat and 193 pounds of muscle, bone and connective tissue. The percent change in lean body weight is 17%, which is highly significant as it was accomplished without a change in diet or exercise regimen.

EXAMPLE 3

A thirty-eighty-year-old healthy male subject who wished to add bodyweight in the form of lean muscle, was treated for seven weeks with two capsule of 500 mg of glutathione, three times per day. The totally daily dose was 3,000 mg of glutathione. The patient weighed 203 pounds (92.3 kg) at the initiation of the treatment, and his percent bodyfat was measured by the caliper method to be 18.5%. This corresponds to 165 pounds of muscle, bone and connective tissue, and 38 pounds of fat. At the end of the seven week treatment period, the subject weighed 241 pounds and his percentage bodyfat was measured to be 15.1%. This corresponds to 36 pounds of fat and 205 pounds of muscle, bone and connective tissue. The percent change in lean body weight is 24.2%, which is highly significant as it was accomplished with no change in diet or exercise regimen.

EXAMPLE 4

A forty-one-year-old healthy male subject who wished to add bodyweight in the form of lean muscle was treated for six weeks with two capsules containing 500 mg of glutathione, twice daily. The totally daily dose was 2,000 mg of glutathione. The patient weighed 212 pounds (96.4 kg) at the initiation of the treatment, and his percent bodyfat was measured by the caliper method to be 17.2%. This corresponds to 176 pounds of muscle, bone and connective tissue, and 36 pounds of fat. At the end of the six week treatment period, the subject weighed 239 pounds and his percentage bodyfat was measured to be 14.9%. This corresponds to 36 pounds of fat and 203 pounds of muscle, bone and connective tissue. The percent change in lean body weight is 15.3%, which is highly significant as it was accomplished with a change in diet or exercise regimen.

What is claimed is:

1. A method for increasing lean bodyweight in a mammal, said method comprising the step of administering, in each 24 hour period, an amount of glutathione or a physiologically acceptable salt or ester thereof effective to increase bodyweight, to a mammal in need of such treatment.

2. The method of claim 1, wherein glutathione or a physiologically acceptable salt thereof is provided in an amount of between about 200 and about 5000 mg.

3. The method of claim 2, wherein glutathione or a physiologically acceptable salt thereof is administered in two to four substantially equal dosages per day, each of said dosages being administered between about three and about eight hours apart.

4. A method for the treatment or prophylaxis of abnormal weight loss in a mammal, said method comprising the step of administering, in each 24 hour period, a therapeutically or prophylactically effective amount of glutathione or a physiologically acceptable salt or ester thereof, to a mammal in need of said treatment or prophylaxis.

5. The method of claim 4, wherein glutathione or a physiologically acceptable salt thereof is provided in an amount of between about 200 and about 5000 mg.

6. The method of claim 5, wherein glutathione or a physiologically acceptable salt thereof is administered in two to four substantially equal dosages per day, each of said dosages being administered between about three and about eight hours apart.

7. The method of claim 4 wherein said weight loss is cachexia.

* * * * *